(12) United States Patent
Marquillas Olondriz et al.

(10) Patent No.: US 9,815,771 B2
(45) Date of Patent: Nov. 14, 2017

(54) METHOD FOR THE SYNTHESIS OF MIRABEGRON AND ITS DERIVATIVES

(71) Applicant: INTERQUIM, S.A., Sant Cugat del Vallès (ES)

(72) Inventors: Francisco Marquillas Olondriz, Barcelona (ES); Estela Riego Arboleya, Sant Feliu de Llobregat (ES)

(73) Assignee: INTERQUIM, S.A., Sant Cugat del Vallès (ES)

( * ) Notice: Subject to any disclaimer, the term of this patent is extended or adjusted under 35 U.S.C. 154(b) by 0 days.

(21) Appl. No.: 15/501,608

(22) PCT Filed: Aug. 5, 2015

(86) PCT No.: PCT/EP2015/068060
§ 371 (c)(1),
(2) Date: Feb. 3, 2017

(87) PCT Pub. No.: WO2016/020440
PCT Pub. Date: Feb. 11, 2016

(65) Prior Publication Data
US 2017/0226045 A1  Aug. 10, 2017

(30) Foreign Application Priority Data
Aug. 6, 2014  (ES) .................................. 201431205

(51) Int. Cl.
*C07C 213/02* (2006.01)
*C07D 277/40* (2006.01)
(52) U.S. Cl.
CPC .......... *C07C 213/02* (2013.01); *C07D 277/40* (2013.01)
(58) Field of Classification Search
CPC ........................... C07C 213/02; C07D 277/40
See application file for complete search history.

(56) References Cited

U.S. PATENT DOCUMENTS

| | | |
|---|---|---|
| 6,346,532 B1 | 2/2002 | Maruyama et al. |
| 7,342,117 B2 | 3/2008 | Kawazoe et al. |

FOREIGN PATENT DOCUMENTS

| | | |
|---|---|---|
| CN | 103232352 A | 8/2013 |
| CN | 103265457 A | 8/2013 |
| CN | 103387500 A | 11/2013 |
| EP | 1 440 969 A1 | 7/2004 |
| JP | 2011-105685 A | 6/2011 |
| WO | WO 99/20607 A1 | 4/1999 |
| WO | WO 03/037881 A1 | 5/2003 |

OTHER PUBLICATIONS

Anonymous, "Preparation of Mirabegron, It's Intermediates, a Crystalline form of Mirabegron and a Crystalline form of Mirabegron Monohydrochloride," IP.com Prior Art Database Technical Disclosure, IPCOM000228561D, Jun. 19, 2013, pp. 1-24 (Total 25 pages).
Imanishi et al., "Discovery of a Novel Series of Biphenyl Benzoic Acid Derivatives as Potent and Selective Human $\beta_3$-Adrenergic Receptor Agonists with Good Oral Bioavailability. Part I," J. Med. Chem., vol. 51, No. 6, 2008 (Published on Web Feb. 29, 2008), pp. 1925-1944.
Written Opinion of the International Searching Authority and International Search Report (forms PCT/ISA/237 and PCT/ISA/210), dated Oct. 14, 2015, for International Application No. PCT/EP2015/068060.

*Primary Examiner* — Shawquia Jackson
(74) *Attorney, Agent, or Firm* — Birch, Stewart, Kolasch & Birch, LLP

(57) ABSTRACT

The present invention refers to a method for the synthesis of a compound of formula (I), solvates, stereoisomers or salts thereof, a key intermediate in the synthesis of Mirabegron by reduction of an amide in the presence of an amine-boranecomplex, wherein the amine is an aniline.

14 Claims, 2 Drawing Sheets

METHOD FOR THE SYNTHESIS OF MIRABEGRON AND ITS DERIVATIVES

FIELD OF THE INVENTION

This invention refers to the synthesis of intermediates key in the synthesis of Mirabegron, and to the synthesis thereof.

STATE OF THE ART

Mirabegron, common name of 2-(2-amino-1,3-thiazol-4-yl)-N-[4-(2-{[(2R)-2-hydroxy-2-phenylethyl]amino}ethyl)phenyl]acetamide, and also commonly previously known as YM-178, is an active substance approved for the treatment of urinary incontinence acting on [beta]3 receptors (now under the trade names Myrbetriq®, Betanis® and Betmiga®). In addition, potential activity has been reported, amongst others, in the treatment of diabetes, obesity or hypertriglyceridemia.

Mirabegron

The methods of preparation described for Mirabegron have mostly used two approaches. A first strategy has first searched for the preparation of the 1-phenyl-2-{[2-(4-[amino]phenyl)ethyl]amino}ethanol subunit (see FIG. 1), hereafter "diaminoalcohol subunit", to which the acid subunit of aminothiazole is coupled in the last stages (see route (a) of FIG. 2). In this strategy the amine groups are protected or free based on the sequence and reagents selected, and in many cases the aromatic nitrogen is in the form of nitro group until its reduction before the coupling with the acid subunit of aminothiazole. A second approach has first searched for the preparation of the N-(p-ethylphenyl)-aminothiazolylacetamide subunit which is then coupled in the final stages with the [beta]-hydroxyethylamine subunit (see route (b) of FIG. 2).

For the diaminoalcohol subunit several methods have been reported. To be noted is the opening of (R)-styrene oxide described in numerous documents such as WO 99/020607 A1 (Yamanouchi Pharmaceutical) or more recently in a version with the amine group protected in CN 103387500 A (Shangai Institute of Pharmaceutical Industry). It is an attractive approach that provides directly the diaminoalcohol subunit. However, (R)-styrene oxide is a CMR 1B compound (carcinogenicity, mutagenicity and toxicity for reproduction), which requires special measures in medicament manufacturing processes. Also searching for the direct formation of the diaminoalcohol subunit in CN 103232352 and CN 103265457 A (Suzhou Uugene Biopharma), it has been considered the reductive amination between (R)-2-amino-1-phenylethanol and the corresponding aldehyde of the p-ethylaniline subunit. This process has however the disadvantage of the cost and the added problem that entails the stable supply of (R)-2-amino-1-phenylethanol. An indirect approach is described in WO 2003/037881 A1 (Yamanouchi Pharmaceutical) preparing the corresponding amide, which is subsequently reduced to amine in the presence of the borane-THF (BH$_3$.THF) complex, using as solvents tetrahydrofuran (THF) and 1,3-dimethyl-2-imidazolidinone (DMI). A similar method is also described in JP 2011-105685 (Astellas Pharma Inc.). This method has several problems. The first is the conversion of the starting material, which is not transformed completely. The cost of DMI is also a problem and mainly its high toxicity, even by simple contact with the skin, and therefore makes it an inadequate co-solvent for industrial scale. The reaction with THF is not completed. The second is the variability in the results mainly due to the instability of BH$_3$. With borane THF/DMI the method described in WO 2003/037881 requires two cooling and heating cycles, that range from −18° C. or −12° C. to reflux temperatures. From an operational viewpoint this markedly complicates the process and affects reproducibility.

Therefore it is necessary to find alternative processes which lead to the formation of the diaminoalcohol subunit for the purpose of developing a synthesis of Mirabegron.

BRIEF DESCRIPTION OF THE INVENTION

The authors have now found an alternative method which allows the obtainment of this key subunit. A first aspect of this invention is a method for the synthesis of a compound of formula (I), solvates, stereoisomers or salts thereof

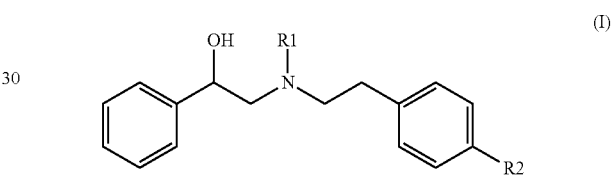

which comprises contacting an amine-borane complex with an [alfa]-hydroxyphenylacetamide of formula (II), solvates, stereoisomers or salts thereof

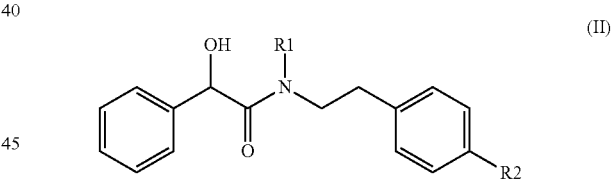

wherein
R$_1$ is hydrogen or an amine or amido protecting group; and
R$_2$ is selected from the group consisting of NO$_2$ and NHR$_3$, wherein R$_3$ is hydrogen or an amine protecting group;
characterized in that the amine of said amine-borane complex is an aniline of formula (III)

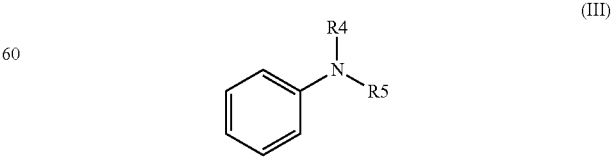

wherein R$_4$ and R$_5$ are independently selected from the linear or branched C$_1$-C$_6$ alkyl groups.

The method of the invention is more robust. In addition to using less toxic reagents, it allows the obtainment of excellent conversions and yields. Furthermore, the authors have found that the result is a product of surprisingly purity and that conversion is almost complete, which facilitates subsequent treatment and isolation. From an operational viewpoint, the method shows advantages and can be operated without the need to perform major temperature changes at facilities commonly used in the manufacture of pharmaceutical active substances.

The method of the invention is therefore an alternative to the synthesis of Mirabegron in any of its amorphous or crystalline forms, and its derivatives. A second aspect of this invention is a method for the synthesis of 2-(2-amino-1,3-thiazol-4-yl)-N-[4-(2-{[(2R)-2-hydroxy-2-phenylethyl]amino}ethyl)phenyl]acetamide comprising preparing a compound of formula (I), solvates, stereoisomers or salts thereof.

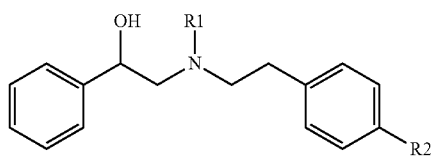

(I)

contacting an amine-borane complex with an [alfa]-hydroxyphenylacetamide of formula (II), solvates, stereoisomers or salts thereof

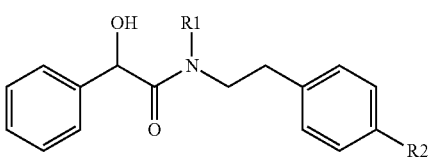

(II)

wherein
$R_1$ is hydrogen or an amine or amido protecting group; and
$R_2$ is selected from the group consisting of $NO_2$ and $NHR_3$, wherein $R_3$ is hydrogen or an amine protecting group;
the amine of said amine-borane group being an aniline of formula (III)

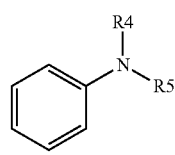

(III)

wherein $R_4$ and $R_5$ are independently selected from the linear or branched $C_1$-$C_6$ alkyl groups;
optionally, perform one or more of the following transformations (i) and (ii):
 (i) reduction of a nitro group to an amine in case $R_2$ is —$NO_2$;
 (ii) deprotection of an amine group;
and couple said compound of formula (I), solvates, stereoisomers or salts thereof, with a compound of formula (VII) or its salts,

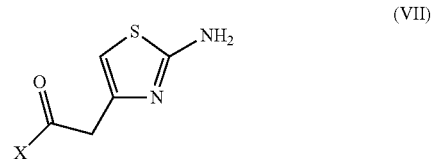

(VII)

wherein X is a leaving group,
the deprotection of an amine group being able to take place before or after the coupling with said compound of formula (VII) or its salts.

DETAILED DESCRIPTION OF THE INVENTION

Definitions

Figure 1:
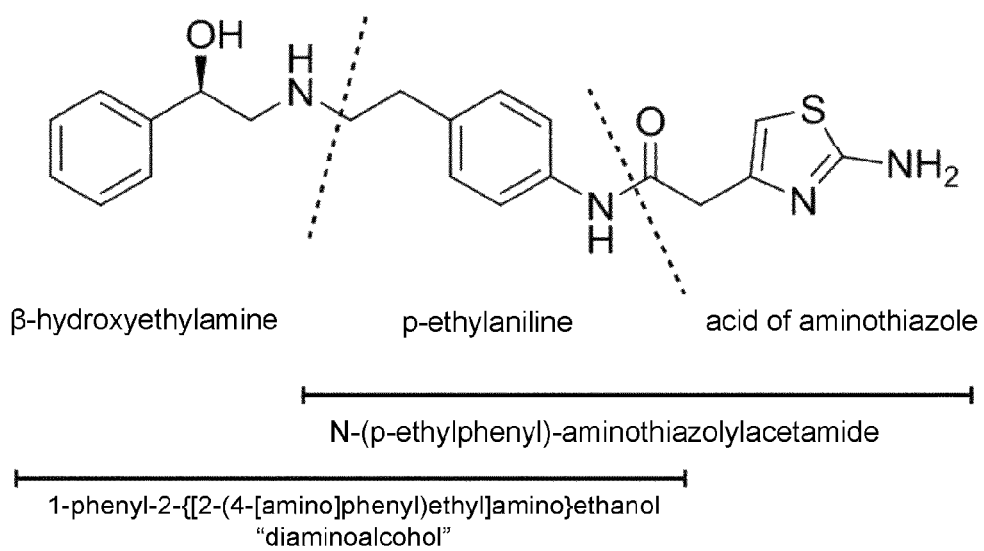
FIG. 1 represents the structure of Mirabegron divided into the subunits (disconnections) which have been used most frequently for its preparation.

The skilled in the art knows the groups which serve as amino protecting or amido protecting groups. According to this invention, by "amino protecting" group, "amido protecting" group or "amine or amido protecting" group are understood those groups with ability to block the reactivity of a nitrogenated function in an amine and/or amide and then can be removed under controlled conditions once its blocking function has been exerted. This type of groups are commonly known by the average skilled in the art and some non limiting examples are
 the groups of formula —C(=O)—O—R', such as for example terc butyloxycarbonyl, benzyloxy carbonyl or p-methoxy benzyloxy carbonyl;
 the groups of formula —$CH_2$—Ar, for example, benzyl; or
 a p-toluenesulfonyl group, amongst others;
 wherein R' is a linear or branched $C_1$-$C_{12}$ alkyl group, and Ar is an aromatic hydrocarbon $C_6$-$C_{12}$ group.

Additional examples can be found in reference texts, such as that of Greene and Wuts' "Protective Groups in Organic Synthesis", John Wiley & Sons, Inc., New York, 4th Ed., 2007.

The term "solvate" according to this invention must be understood to mean any form of the compounds in reference to which it is mentioned which are linked to another molecule (most probably a polar solvent) through a non-covalent bond. Non-limiting examples of molecules which may form a solvate with the compounds described in this invention are water (hydrates), alcohols, such as for example, methanol or isopropanol; esters such as ethyl acetate;

ketones as acetone or methyl isobutyl ketone; and nitriles such as acetonitrile. According to a particular embodiment, said solvate is a hydrate.

An "stereoisomer" in this patent application refers to compounds formed by the same atoms linked by the same sequence of bonds, but which have different three-dimensional structures which are not interchangeable.

The term "salt" refers to any form of compounds in reference to which it is mentioned which assume an ionic form or are charged and coupled with a counterion (a cation or an anion) or are in dissolution. For instance, salts of the compounds mentioned here can be acid addition salts, base addition salts or metal salts, and can be synthesized from the original compound containing a basic or acid moiety by conventional chemical methods. Such salts are generally prepared, for example, by reacting the free base or acid forms of these compounds with an stechiometric amount of appropriate acid or base in water or in an organic solvent or in a mixture of both. Non-aqueous media, as ether, ethyl acetate, ethanol, isopropanol or acetonitrile. are generally preferred. Examples of acid addition salts include mineral acid addition salts, such as, for example, hydrochloride, hydrobromide, hydroiodide, sulfate, nitrate, phosphate and organic acid addition salts such as, for example, acetate, maleate, fumarate, citrate, oxalate, succinate, tartrate, malate, mandelate, methanesulfonate and p-toluenesulfonate. Examples of base addition salts include inorganic salts such as for example ammonium and organic alkali salts such as for example ethylenediamide, ethanolamine, N,N-dialkylenethanolamine, triethanolamine, glucamine and basic amino acid salts. Examples of metal salts include, for example, sodium, potassium, calcium, magnesium, aluminum and lithium salts.

"Alkyl" refers to a linear or branched hydrocarbon chain radical consisting of carbon and hydrogen atoms containing no unsaturation, which has the indicated number of carbon atoms, and which is bound to the rest of the molecule by a single bond, for example, methyl, ethyl, n-propyl, i-propyl, n-butyl, t-butyl, n-pentyl, etc.

By "complex" are understood molecules in which a donor seeks to donate a couple of free electrons and an acceptor has the ability to accept said couple of electrons.

By "leaving group" is understood in this invention any group that is joined to the carbonylic carbon atom —(C=O), and which is displaced in the reaction. Therefore, these are groups that, together with the carbonylic carbon atom —(C=O) to which they are linked, form an acid or an acid derivative in the compounds of formula (VII) of the invention and facilitate the coupling with the compounds of formula (I). The skilled in the art has at his disposal a wide range of these groups adequate to perform the coupling. Different groups have been used in the state of the art. For example, acids, esters or acid halides in WO 99/020607 A1, or in WO 2003/037881 A1. In the case of acids, the reaction generally requires the use of activators such as for example carbodiimides. In a preferred embodiment of the invention, the group X is selected from the group consisting of —OH, —O—$C_1$-$C_6$ alkyl, and halogen.

Reduction of the Amide Group

This invention allows to prepare any compound of formula (I). The most efficient route of preparation of Mirabegron is a priori that in which $R_2$ is a nitro group, although it is possible to perform the reaction of the invention on [alpha]-hydroxyphenylacetamide of formula (II) wherein $R_2$ is an amine group or an amine group protected with an amine protecting group. In view of the foregoing, in a preferred embodiment of the invention $R_2$ is $NO_2$. According to another preferred embodiment, $R_1$ is hydrogen and $R_2$ is $NO_2$. Preferably the compound of formula (I) is (R)-1-phenyl-2-{[2-(4-nitrophenyl)ethyl]amino}ethanol hydrochloride. According to another preferred embodiment, [alpha]-hydroxyphenylacetamide of formula (II) is (R)-2-hydroxy-N-[2-(4-nitrophenyl)ethyl]-2-phenylacetamide.

The reducing agent used in this invention is a complex formed by a borane and an aniline of formula (III)

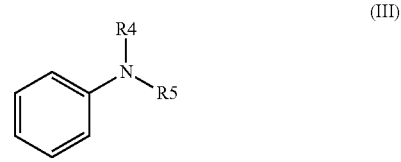

wherein $R_4$ and $R_5$ which are independently selected from the linear or branched $C_1$-$C_6$ alkyl groups.

These ones allow to perform the process more robustly while providing excellent conversions and yields. These anilines of formula (Ill) are commercially accessible and their handling does not require special safety measures. According to a preferred embodiment, $R_4$ and $R_5$ are independently selected from the linear or branched $C_2$-$C_4$ alkyl groups and are preferably ethyl or isopropyl. According to a particular embodiment, the amine-borane complex is N,N-diethylaniline borane or N-ethyl-N-isopropylaniline borane. More preferably, the amine-borane complex is N,N-diethylaniline borane.

According to a particular embodiment, the method of the invention comprises reacting (R)-2-hydroxy-N-[2-(4-nitrophenyl)ethyl]-2-phenylacetamide with a complex formed by a borane and an aniline of formula (Ill) to yield (R)-1-phenyl-2-{[2-(4-nitrophenyl)ethyl]amino}ethanol (see Scheme 1).

Scheme 1

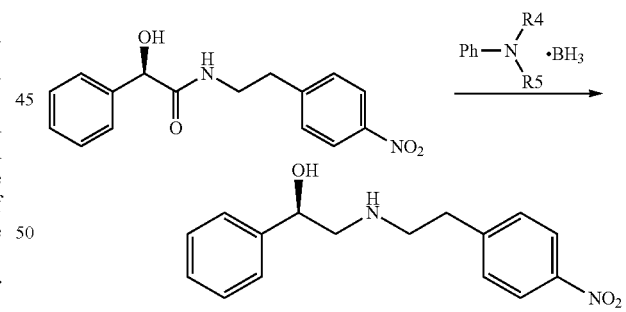

The reaction conditions may vary in a wide range while maintaining the advantages of the present invention. For example, it is possible to operate in a wide range of temperatures, for example between 0 and 100° C., according to a particular embodiment temperatures between 40° C. and 70° C. can be used. According to a particular embodiment, the components are mixed at a temperature between 0° C. and 60° C. and then the reaction mixture is heated at a temperature higher than the initial, for example, the reflux temperature of tetrahydrofuran. The reaction also admits a wide variety of solvents, although those most commonly used are linear or cyclic ethers, for example, diethyl ether, t-butylmethylether or tetrahydrofuran or aliphatic or aromatic hydrocarbons, for example, toluene, xylene, cyclohexane or mixtures thereof, for example, mixtures of toluene and tetrahydrofuran.

Therefore, this invention allows to operate easily without the need of large temperature variations. The components are mixed and the reaction is allowed to proceed, if necessary, with heat application. In search for alternatives for this reaction, the inventors have not found, in addition to the abovementioned patent application WO 2003/037881 A1, any evidence in the literature on the reactivity of linear [alfa]-hydroxyamides vs the reduction with boranes or with amine-boranes in particular, and the results obtained with the amine-boranes of formula (III) provide an excellent, more efficient alternative for the industrial synthesis of Mirabegron.

Therefore, to obtain Mirabegron or any of its derivatives from the compounds of formula (I), in addition to the coupling with the compound of formula (VII), only the steps of deprotecting the amine ($R_1$=—H; $R_2$=—$NH_2$) group(s) and/or transformation of a nitro group into amine or protected amine are required, if necessary.

These transformations are performed by methods known in the state of the art.

The deprotection of the amine groups by removal of the nitrogen protecting groups is performed under conditions that change depending on the protecting group chosen, conditions which are widely known and which are described in reference texts, such as for example the abovementioned Greene and Wuts' "Protective Groups in Organic Synthesis", John Wiley & Sons, Inc., New York, 4th Ed., 2007. Such deprotection can take place at different times based on, for example, the nature of the nitrogen protecting group or other subsequent reaction conditions. Therefore, according to a particular embodiment, the sequence of reactions followed is firstly the reduction of the amide group to amine to obtain the compounds of formula (I) wherein $R_1$ is a protecting group, followed by deprotection to obtain a compound of formula (I) wherein $R_1$ is hydrogen to finally perform the coupling with the compound of formula (VII). In another possible embodiment of the invention the order of deprotection and coupling are inverted so that firstly the reduction of the amide group to amine is performed to obtain the compounds of formula (I) wherein $R_1$ is a protecting group, then the coupling is performed with the compound of formula (VII), to finally deprotect the amine. It is also possible that the group $R_2$ in the compounds of formula (I) or (II) is —$NHR_3$, being $R_3$ a protecting group and therefore being it necessary to deprotect in order to obtain Mirabegron. Said deprotection can be also performed at different times of the process. For example, it is possible to couple a compound of formula (VII) with a compound of formula (I) wherein $R_2$ is $NHR_3$, $R_3$ being a protecting group, to deprotect said amine group once the coupling is performed. Alternatively, if a compound of formula (I) is present, wherein $R_2$ is $NHR_3$, $R_3$ being a protecting group, it can firstly be deprotected to obtain a compound of formula (I) wherein $R_2$=—$NH_2$, to then perform the coupling with the compound of formula (VII).

In addition, if necessary, as part of the sequence described above, an additional stage of protection and subsequent deprotection can be carried out of any reactive group present in a compound of formula (I), for example, of the hydroxyl or the amine ($R_1$=H) group, For example, as described in IP.COM000228561D before the coupling reaction of a compound of formula (I) with the compound of formula (VII), the hydroxyl group and the amine group of a compound of formula (I) can be protected simultaneously, by the formation of an oxazolidinone, which is hydrolyzed once the reaction has proceeded.

The reduction of the nitro group to an amine group admits different conditions known in the state of the art. Conditions which have already been tested for the synthesis of Mirabegron are described in WO 99/20607 A1, WO 2003/037881 A1, or CN 103387500 A and include the catalytic hydrogenation in the presence of a palladium catalyst. For example, using palladium on carbon in an appropriate solvent, typically methanol. Other conditions known for the transformation of the nitro group into amine are also possible, such as, for example, the treatment with zinc or tin in acidic medium. See, for example, section 9-47 of "Advanced Organic Chemistry: reactions, mechanisms and structures", March, J., 4th edition, Wiley-interscience, for further reaction conditions. According to a preferred embodiment, the reduction of a nitro group to amine is performed by catalytic hydrogenation. Other conditions for the reduction are possible, and the skilled in the art can make changes in the reagents and conditions according to the present invention.

Therefore, in a preferred embodiment, a compound of formula (I) obtained according to the method of this invention, wherein $R_2$ is —$NO_2$, is transformed into a compound of formula (I) wherein $R_2$ is —$NH_2$ in the presence of hydrogen and a catalyst, preferably a palladium catalyst.

One-Pot Reduction of the Amide and the Nitro Group

In addition, the purity at which the compounds of formula (I) are obtained after the reduction stage of [alfa]-hydroxyphenylacetamide of formula (II) under the conditions of this invention allows to couple said stage with the reduction of the nitro group without the need to isolate ("one-pot") the intermediate product. The inventors have discovered that this coupled process surprisingly leads to a total conversion of the starting material. Therefore, following the method described above, it is possible to treat an [alfa]-hydroxyphenylacetamide of formula (II), wherein $R_2$ is —$NO_2$, with an amine-borane complex wherein the amine is an aniline of formula (III) to give a compound of formula (I) wherein $R_2$ is —$NO_2$, and then, without isolating said compound of formula (I), perform the reduction of the nitro group to obtain a compound of formula (I), solvates, stereoisomers or salts thereof, wherein $R_2$ is —$NH_2$.

According to this embodiment, the conditions to reduce the nitro group to amine can be that usually employed in this type of transformations, preferably in the presence of hydrogen and a palladium catalyst.

In a particular embodiment, the one-pot method involves reducing the nitro group in the presence of the Pearlman's catalyst (Pd(OH)$_2$), an alcohol and the amine-borane complex wherein the amine is an aniline of formula (III). These conditions allow the formation in situ of hydrogen, which entails many advantages from an operational viewpoint, which in combination with the fact that it can be coupled to the reduction of [alfa]-hydroxyphenylacetamide of formula (II) in a one-pot method, makes the process of the invention particularly advantageous. Due to operational reasons the aniline of formula (III) is preferably the same as that used in the previous stage. In a particular embodiment the alcohol is a carbon from 1 to 6 carbon atoms, preferably 1 to 4. Non-limiting examples are methanol, ethanol or isopropanol.

In a particular embodiment, $R_1$ is hydrogen and the reduction of the nitro group is performed in the presence of the Pearlman's catalyst, methanol, and the same amine-borane complex used in the reduction stage of [alfa]-hydroxyphenylacetamide of formula (II), as shown below in Scheme 2.

Scheme 2

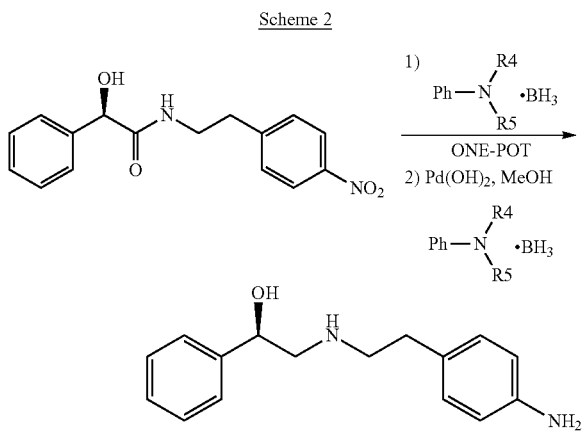

Synthesis of Mirabegron

Figure 2:
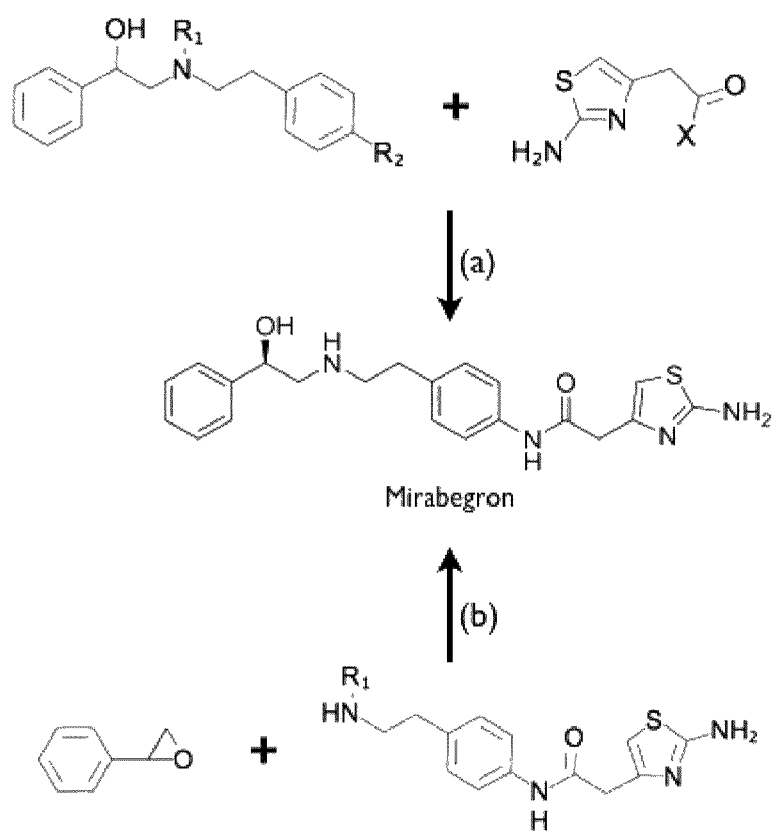
FIG. 2 shows the two most used strategies for the synthesis of Mirabegron. The first (route (a)) firstly prepares the 1-phenyl-2-{[2-(4-[amino]phenyl)ethyl]amino}ethanol subunit ("diaminoalcohol subunit"), which is then coupled with the acid subunit of aminothiazole. The second approach (route (b)) firstly prepares the N-(p-ethylphenyl)-aminothiazolylacetamide subunit which is then coupled in the final stages with the [beta]-hydroxyethylamine subunit.

The diaminoalcohol subunit is therefore a key intermediate in the synthesis of Mirabegron, for which different methods of synthesis have been described in the literature which entail essentially the coupling of a compound of formula (VII) or its salts (i.e., the acid subunit of aminothiazole—FIG. 2)

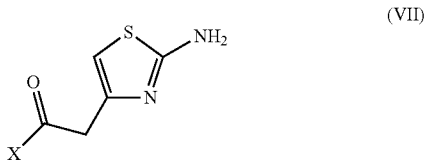

(VII)

wherein X is a leaving group.

For example, in WO 99/20607 A1 Mirabegron is obtained by coupling a compound of formula (I), wherein $R_1$ is a protecting group, and $R_2$ an amine group, with a compound of formula (VII), similarly to that described in the reference example 5. The resulting compound is deprotected in order to provide Mirabegron. Another example can be found in WO 2003/037881 A1, where a similar method is described which couples the hydrochloride to a compound of formula (I), wherein $R_1$ is hydrogen, and $R_2$ is an amino group, with a compound of formula (VII) wherein X is —OH to give the [beta] form of Mirabegron. Similar reactions have also been reproduced in CN 103387500 A and CN 103232352 A.

In a particular embodiment, the compounds of formula (I) are transformed into 2-(2-amino-1,3-thiazol-4-yl)-N-[4-(2-{[(2R)-2-hydroxy-2-phenylethyl]amino}ethyl)phenyl]acetamide (Mirabegron).

According to another particular embodiment, the method for obtaining Mirabegron according to this invention comprises (a) contacting said amine-borane complex with said [alfa]-hydroxyphenylacetamide of formula (II), solvates, stereoisomers or salts thereof, wherein $R_2$ is —$NO_2$, to provide the corresponding compound of formula (I) wherein $R_2$ is —$NO_2$, solvates, stereoisomers or salts thereof; (b) reducing said —$NO_2$ group to —$NH_2$ in the presence of hydrogen and a catalyst and (c) coupling the resulting compound of formula (I), solvates, stereoisomers or salts thereof, with this compound of (VII) or its salts.

According to another particular embodiment, the method for obtaining Mirabegron according to the present invention comprises (a) contacting said amine-borane complex with (R)-2-hydroxy-N-[2-(4-nitrophenyl)ethyl]-2-phenylacetamide, solvates, stereoisomers or salts thereof, to provide (R)-1-phenyl-2-{[2-(4-nitrophenyl)ethyl]amino}ethanol, solvates, stereoisomers or salts thereof; (b) reducing the nitro group by catalyst hydrogenation to give (R)-2-(4-aminophenylethylamine)-1-phenylethanol, solvates, stereoisomers or salts thereof, and (c) coupling said (R)-2-(4-aminophenylethylamine)-1-phenylethanol, solvates, stereoisomers or salts thereof, with said compound of formula (VII) or its salts.

The skilled in the art will understand that the preferences related to the transformation of the compounds of formula (II) into compounds of formula (I) are applicable both in the case of this transformation as considered individually and those processes in which it is associated with other transformations, for example, the synthesis of Mirabegron.

EXAMPLES

Example 1: Preparation of (R)-1-phenyl-2-{[2-(4-nitrophenyl)ethyl]amino}ethanol Hydrochloride from (R)-2-hydroxy-N-[2-(4-nitrophenyl)ethyl]-2-phenylacetamide N,N-diethylaniline borane (DEANB, 2 eq) complex was added to a solution of (R)-2-hydroxy-N-[2-(4-nitrophenyl)ethyl]-2-phenylacetamide (reference) in tetrahydrofuran (5 L/Kg) at 50° C. and the mixture was heated to reflux temperature for 6 h. After this time, the content of unreacted (R)-2-hydroxy-N-[2-(4-nitrophenyl)ethyl]-2-phenylacetamide was checked by HPLC, it being only 0.74%.

Methanol (2 L/Kg) and concentrated hydrochloric acid (2 L/Kg) were added after cooling at room temperature, and the reaction mixture was heated for 1 h. Deionized water was added (7 L/Kg) and the organic solvents were distilled. After adding ethyl acetate (10 L/Kg) on the residue of distillate, the pH of the sample was adjusted to 8.5-9.5, after which the phases were separated. The organic phase was washed with deionized water (5 L/Kg) and concentrated in vacuo. The residue was dissolved in isopropanol (4 L/Kg) and was treated with concentrated hydrochloric acid (0.2 L/Kg) at 40° C. The obtained suspension was stirred overnight at room temperature, filtered and washed with isopropanol (2×2.5 L/Kg). The solid was dried in vacuo at 40-45° C. Purity: 99.2% (HPLC).

Reference Example 2 of WO 2003/037881 A1 (Comparative)

Onto a mixture of 5 g of (R)-2-hydroxy-N-[2-(4-nitrophenyl)ethyl]-2-phenylacetamide, 15 mL of anhydrous 1,3-dimethyl-2-imidazolidinone and 15 mL of anhydrous tetrahydrofuran at −18° C., were added dropwise 33.0 g of a 1 M solution of borane-tetrahydrofuran, without the temperature exceeding −7° C. Once the addition was completed, the mixture was heated at 70° C. and kept for 5 h. After this time had elapsed, the content of unreacted (R)-2-hydroxy-N-[2-(4-nitrophenyl)ethyl]-2-phenylacetamide was checked by HPLC, it being 5.1%.

Example 2: Preparation of (R)-2-(4-aminophenylethylamine)-1-phenylethanol Hydrochloride from (R)-1-phenyl-2-{[2-(4-nitrophenyl)ethyl]amino}ethanol Hydrochloride by Hydrogenation A mixture of (R)-1-phenyl-2-{[2-(4-nitrophenyl)ethyl]amino}ethanol hydrochloride (reference), methanol (10

L/Kg) and 5% Pd/C (20% by weight) was stirred for 3 h under a hydrogen atmosphere. The HPLC analysis of the reaction mixture showed a complete conversion. The reaction mixture was filtered and the filtrate was concentrated in vacuo, obtaining a solid.

Example 3: Preparation of (R)-2-(4-aminophenyl-ethylamine)-1-phenylethanol from (R)-1-phenyl-2-{[2-(4-nitrophenyl)ethyl]amine}ethanol by Hydrogen Generation by Methanolysis of the N,N-diethylaniline Borane Complex A mixture of (R)-1-phenyl-2-{[2-(4-nitrophenyl)ethyl]amine}ethanol (reference), methanol (5 L/Kg), and Pearlman's catalyst (10% by weight) was treated with DEANB (2 eq) at room temperature. The HPLC analysis of the reaction mixture showed a conversion.

Example 4: One-Pot Preparation of (R)-2-(4-amino-phenylethylamine)-1-phenylethanol from (R)-2-hydroxy-N-[2-(4-nitrophenyl)ethyl]-2-phenylacetamide N,N-diethylaniline borane complex (DEANB, 2 eq) was added onto a solution of (R)-2-hydroxy-N-[2-(4-nitrophenyl)ethyl]-2-phenylacetamide (reference) in tetrahydrofuran (5 L/Kg) at 50° C., and then the mixture was heated at reflux temperature for 6 h. Methanol (2 L/Kg) and concentrated hydrochloric acid (2 L/Kg) were added after cooling at room temperature, and the reaction mixture was heated for 1 h. Deionized water (7 L/Kg) was added, and the organic solvents were distilled. After adding ethyl acetate (10 L/Kg) onto the distilled residue, the pH of the sample was adjusted to 8.5-9.5, after which the phases were separated. The organic phase was washed with deionized water (5 L/Kg) and concentrated in vacuo. The residue was dissolved in methanol (5 L/Kg) followed by the addition of Pearlman's catalyst (Pd(OH)$_2$/C—10% by weight). DEANB (1.5 equivalent) was added dropwise for 30 minutes at room temperature. The HPLC analysis of the reaction mixture showed total conversion.

Example 5: One-Pot Preparation of (R)-2-(4-amino-phenylethylamine)-1-phenylethanol from (R)-2-hydroxy-N-[2-(4-nitrophenyl)ethyl]-2-phenylacetamide N,N-diethylaniline borane complex (DEANB, 3 eq) was added onto a solution of (R)-2-hydroxy-N-[2-(4-nitrophenyl)ethyl]-2-phenylacetamide (reference) in tetrahydrofuran (5 L/Kg) at 50° C. and the mixture was heated at reflux temperature for 3 h. Toluene was added (4 L/Kg) and tetrahydrofuran was distilled from the reaction mixture. The resulting residue was gradually added on a suspension of Pearlman's reagent (Pd(OH)$_2$/C—10% by weight) in methanol (4 L/Kg) at room temperature. After checking by HPLC a 47% conversion, 1 equivalent of DEANB was added and the mixture was stirred at room temperature until it reached the total conversion.

The invention claimed is:

1. A method for the synthesis of a compound of formula (I), solvates, stereoisomers or salts thereof,

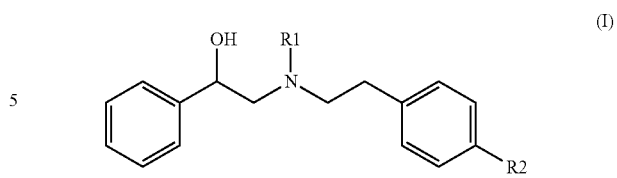

which comprises contacting an amine-borane complex with an [alpha]-hydroxyphenylacetamide of formula (II), solvates, stereoisomers or salts thereof

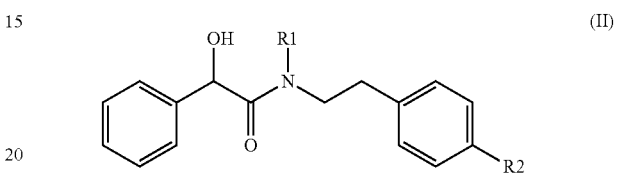

wherein
$R_1$ is hydrogen or an amine or amido protecting group; and
$R_2$ is $NO_2$ or $NHR_3$, wherein $R_3$ is hydrogen or an amine protecting group;
characterized in that the amine of said amine-borane complex is an aniline of formula (III)

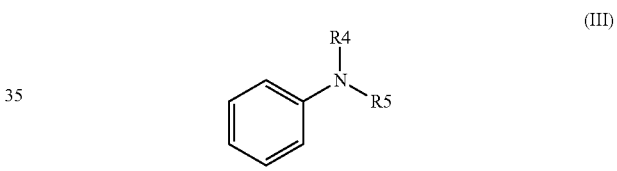

wherein $R_4$ and $R_5$ are independently selected from the linear or branched $C_1$-$C_6$ alkyl groups.

2. The method according to claim 1, characterized in that $R_4$ and $R_5$ are independently selected from the linear or branched $C_2$-$C_4$ alkyl groups.

3. The method according to claim 1, characterized in that $R_4$ and $R_5$ are independently selected from the ethyl and isopropyl groups.

4. The method according to claim 1, characterized in that said amine-borane complex is N,N-diethylaniline borane or N-ethyl-N-isopropylaniline borane.

5. The method according to claim 1, characterized in that $R_2$ is $NO_2$.

6. The method according to claim 1, characterized in that $R_1$ is hydrogen and $R_2$ is $NO_2$.

7. The method according to claim 1, characterized in that said compound of formula (I) is (R)-1-phenyl-2-{[2-(4-nitrophenyl)ethyl]amino}ethanol hydrochloride.

8. The method according to claim 1, characterized in that said [alfa]-hydroxyphenylacetamide of formula (II) is (R)-2-hydroxy-N-[2-(4-nitrophenyl)ethyl]-2-phenylacetamide.

9. The method according to claim 1, characterized in that said compound of formula (I) wherein $R_2$ is $NO_2$ is transformed into a compound of formula (I) wherein $R_2$ is —$NH_2$ in the presence of hydrogen and a catalyst.

10. The method according to claim 9, characterized in that said transformation is performed without isolating the compound of formula (I).

11. The method according to claim 1, characterized in that said compound of formula (I) is transformed into 2-(2-amino-1,3-thiazol-4-yl)-N-[4-(2-[(2R)-2-hydroxy-2-phenyl ethyl]amino ethyl)phenyl]acetamide.

12. A method for the synthesis of 2-(2-amine-1,3-thiazol-4-yl)-N-[4-(2-{[(2R)-2-hydroxy-2-phenylethyl]amino}ethyl)phenyl]acetamide which comprises preparing a compound of formula (I), solvates, stereoisomers or salts thereof

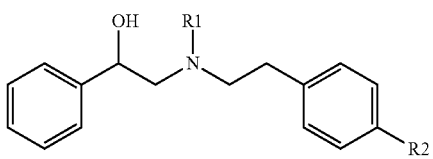
(I)

contacting an amine-borane complex with an [alpha]-hydroxyphenylacetamide of formula (II), solvates, stereoisomers or salts thereof

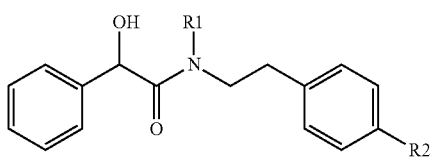
(II)

wherein $R_1$ is hydrogen or an amine or amido protecting group; and $R_2$ is $NO_2$ or $NHR_3$, wherein $R_3$ is hydrogen or an amine protecting group;

the amine of said amine-borane complex being an aniline of formula (III)

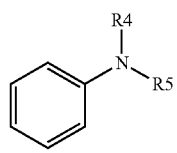
(III)

wherein $R_4$ and $R_5$ are independently selected from the linear or branched $C_1$-$C_6$ alkyl groups;

optionally, perform one or more of the following transformations (i) and (ii):

(i) reduction of a nitro group to an amine in case $R_2$ is —$NO_2$;

(ii) deprotection of an amine group;

and couple said compound of formula (I), solvates, stereoisomers or salts thereof, with a compound of formula (VII) or its salts,

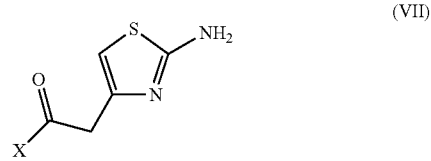
(VII)

wherein X is a leaving group, the deprotection of an amine group (ii) being able to take place before or after the coupling with said compound of formula (VII) or its salts.

13. The method according to claim 12, comprising (a) contacting said amine-borane complex with (R)-2-hydroxy-N-[2-(4-nitrophenyl)ethyl]-2-phenylacetamide, solvates, stereoisomers or salts thereof, to provide (R)-1-phenyl-2-{[2-(4-nitrophenyl)ethyl]amino}ethanol, solvates, stereoisomers or salts thereof; (b) reduce the nitro group in the presence of hydrogen and a catalyst to give (R)-2-(4-aminophenylethylamine)-1-phenylethanol, solvates, stereoisomers or salts thereof, and (c) couple said (R)-2-(4-aminophenylethylamine)-1-phenylethanol, solvates, stereoisomers or salts thereof, with said compound of formula (VII) or its salts.

14. The method according to claim 12, wherein X is —OH, —O—$C_1$-$C_6$ alkyl or halogen.

* * * * *